(12) United States Patent
Shimp

(10) Patent No.: US 10,368,995 B2
(45) Date of Patent: Aug. 6, 2019

(54) METHODS FOR CARBONATE SURFACE COATING AND RELATED BONE VOID FILLER COMPOSITIONS

(71) Applicant: CaP Biomaterials, LLC, East Troy, WI (US)

(72) Inventor: Lawrence A. Shimp, Burlington, WI (US)

(73) Assignee: CaP Biomaterials, LLC, East Troy, WI (US)

( * ) Notice: Subject to any disclaimer, the term of this patent is extended or adjusted under 35 U.S.C. 154(b) by 0 days.

(21) Appl. No.: 15/812,847

(22) Filed: Nov. 14, 2017

(65) Prior Publication Data

US 2018/0133014 A1    May 17, 2018

Related U.S. Application Data

(60) Provisional application No. 62/421,541, filed on Nov. 14, 2016.

(51) Int. Cl.
| | |
|---|---|
| *A61F 2/30* | (2006.01) |
| *A61L 27/24* | (2006.01) |
| *A61L 27/32* | (2006.01) |
| *A61L 27/36* | (2006.01) |
| *A61L 27/56* | (2006.01) |
| *A61L 27/30* | (2006.01) |
| *A61L 27/50* | (2006.01) |
| *A61L 31/00* | (2006.01) |
| *A61L 31/04* | (2006.01) |
| *A61L 31/08* | (2006.01) |
| *A61L 31/14* | (2006.01) |
| *A61F 2/28* | (2006.01) |
| *A61L 27/54* | (2006.01) |
| *A61L 27/58* | (2006.01) |

(52) U.S. Cl.
CPC .......... *A61F 2/30767* (2013.01); *A61L 27/24* (2013.01); *A61L 27/306* (2013.01); *A61L 27/32* (2013.01); *A61L 27/3608* (2013.01); *A61L 27/50* (2013.01); *A61L 27/56* (2013.01); *A61L 31/005* (2013.01); *A61L 31/044* (2013.01); *A61L 31/088* (2013.01); *A61L 31/14* (2013.01); *A61L 31/146* (2013.01); *A61F 2002/2835* (2013.01); *A61L 27/54* (2013.01); *A61L 27/58* (2013.01); *A61L 2420/02* (2013.01); *A61L 2430/02* (2013.01)

(58) Field of Classification Search
CPC .... A61F 2/30767; A61L 31/146; A61L 27/32; A61L 27/56; A61L 27/24; A61L 27/3608; A61L 2420/02
See application file for complete search history.

(56) References Cited

U.S. PATENT DOCUMENTS

| | | | |
|---|---|---|---|
| 2,164,943 A | 7/1939 | Roderick | |
| 6,114,414 A | 9/2000 | Daly et al. | |
| 6,426,114 B1 | 7/2002 | Troczynski et al. | |
| 7,074,223 B2 * | 7/2006 | Axen | A61L 27/30 427/180 |
| 2013/0251689 A1 | 9/2013 | Van Dyke et al. | |

OTHER PUBLICATIONS

International Search Report and Written Opinion for PCT/US2017/061598 dated Feb. 19, 2018, 15 pages.

* cited by examiner

*Primary Examiner* — Carlos A Azpuru
(74) *Attorney, Agent, or Firm* — Reinhart Boerner Van Deuren s.c.

(57) ABSTRACT

Bone void filler compositions and methods for preparation to provide substrates with carbonate surface coatings to promote bone growth.

17 Claims, No Drawings

METHODS FOR CARBONATE SURFACE COATING AND RELATED BONE VOID FILLER COMPOSITIONS

This application claims priority to and the benefit of application Ser. No. 62/421,541 filed on Nov. 14, 2016—the entirety of which is incorporated herein by reference.

BACKGROUND OF INVENTION

Bone void fillers (BVF) are useful as scaffolds for bone healing. A scaffold conducts bone growth over gaps too large for bone to bridge by itself, and can accelerate the rate of bone healing in voids of all sizes. Calcium salts are generally recognized as a class of BVF materials. For instance, calcium phosphate salts are commonly used as they are related to hydroxyapatite (HA), which is a form of calcium phosphate in bone material. Calcium sulfate and calcium carbonate, while not containing phosphate, are also useful as BVF materials.

The bone healing process consists of three major stages: removal of damaged bone debris, growth of new bone, and final bone remodeling. Specialized bone cells called osteoclasts participate in the removal of bone debris and in resorbing mature bone to aid in remodeling. Other cells called osteoblasts grow new bone onto a collagen structure formed by fibroblasts or onto already existing mineralized surfaces. The sequence of bone growth and remodeling is controlled by specific proteins of the general class of growth factors.

Successful scaffold materials generally allow direct attachment of osteoblasts to their surfaces, and the scaffolds are then eventually remodeled and finally replaced by bone. However, the remodeling rate must not be faster than the rate of bone growth or the bone may not heal. Conventional scaffold materials are especially suited to supporting osteoblast activity and are intended to last until bone has fully bridged any gaps.

Non-cemented implants intended for use in bone can also benefit from an osteoconductive surface. Such implants include joint prostheses, screws, plates, spinal stabilizing devices, etc. Such metal or polymeric implants (in particular, prostheses) are often coated with HA to provide a more bone compatible surface. (Even the metal of such an implant can be specified to be more bone compatible by, for example, using a titanium alloy instead of a cobalt chrome alloy.) An HA plasma sprayed coating can facilitate bone on-growth onto the implant with long-term stability occurring as the coating remodels until the bone is attached directly to the implant surface.

Calcium carbonate applied to an HA coating can speed up the natural remodeling process and achieve final stability sooner than otherwise possible. This can be an advantage especially in dental applications where a slightly porous HA coating can more easily become infected, as compared to a coating in a deep internal location such as a hip implant. As a result, rapid remodeling of the HA coating lessens the likelihood of failure due to infection.

A perceived drawback to use of calcium carbonate is the tendency to stimulate osteoclast activity. This stimulation is probably due to the relatively rapid dissolution of calcium carbonate compared to calcium phosphates and the accompanying release of calcium ions. However, as the active osteoclasts break down bone they liberate osteoblast stimulating growth factors from the bone and, in doing so, can actually bring about more rapid bone healing. But calcium carbonate is not as effective in large voids because it is too soluble. The solubility means calcium carbonate may not be stable enough to function as a scaffold long enough for the bone gap to be bridged. As an alternate approach, calcium carbonate granules or powder can be mixed with a more stable, conventional BVF material, but the calcium carbonate component of such mixtures tends to separate and segregate, thereby inducing concerns of the sort outlined above.

SUMMARY OF THE INVENTION

In light of the foregoing, it is an object of the present invention to provide bone void filler compositions and/or methods for their preparation, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a calcium carbonate bone void filler composition with sufficient stability to promote growth in a bone tissue gap.

It can be an object of the present invention to provide a scaffold comprising such a calcium carbonate composition to conduct and facilitate bone growth over gaps otherwise too large for proper bone healing.

It can be an object of the present invention, alone or in conjunction with one or more of the preceding objectives, to provide a methodology for the preparation of such bone void filler scaffold compositions for use in bone healing.

Other objects, features, benefits and advantages of the present invention will be apparent from this summary and the following descriptions of certain embodiments, and will be readily apparent to those skilled in the art having knowledge of bone growth and healing processes and compositions and related methodologies for promoting the same. Such objects, features, benefits and advantages will be apparent from the above as taken into conjunction with the accompanying examples, data and all reasonable inferences to be drawn therefrom.

In part, the present invention can be directed to a method of preparing discrete calcium carbonate particles on a substrate surface. Such a method can comprise providing a carbonatable calcium precursor component and applying such a precursor component to a bone void filler substrate; and contacting such a substrate with a carbon dioxide source to convert at least a portion of such an applied carbonatable calcium precursor component to calcium carbonate, and provide calcium carbonate particles on such a substrate. In certain embodiments, such a carbonatable calcium precursor component can be, without limitation, selected from calcium chloride, calcium oxide and calcium acetate. Such a precursor can be applied by procedures selected from dipping or soaking such a substrate in an aqueous solution of such a carbonatable calcium precursor component and spraying such a substrate therewith. Regardless, such a carbon dioxide source can be selected from gaseous carbon dioxide, liquid supercritical carbon dioxide and sodium carbonate. In certain such embodiments, contact with carbon dioxide can, optionally, be in the presence of water, such a water presence as can be selected from atmospheric water vapor and water applied to such a substrate.

In certain embodiments, such a carbonatable calcium precursor can be treated with an alkali metal hydroxide to provide calcium hydroxide. In certain such embodiments, such a treatment can be with sodium hydroxide. Carbonation with a carbon dioxide source can then convert calcium hydroxide to calcium carbonate. Regardless, such a bone void filler substrate can comprise a material known to those skilled in the art, such a material as can be selected from calcium salts, including but not limited to calcium phosphates, collagen-based materials and organic bone, polymers, metals and metal alloys and combinations thereof, in a physical form such as but not limited to particles, blocks, specifically-molded or machined implants, collagen sponges or strips and allograft or xenograft tissues.

In part, the present invention can also be directed to a method of preparing a calcium carbonate surface coating. Such a method can comprise providing a carbonatable calcium precursor component selected from calcium chloride, calcium oxide and calcium acetate, and applying such a precursor component to the surface of a bone void filler substrate; and contacting such a substrate with a carbon dioxide source, optionally in the presence of water, to convert at least a portion of such an applied carbonatable calcium precursor component to calcium carbonate, and provide a coating of dispersed calcium carbonate particles on such a substrate surface. Such a precursor can be applied by procedures selected from dipping or soaking such a substrate in an aqueous solution of such a carbonatable calcium precursor component and spraying such a substrate therewith. Regardless, such a carbon dioxide source can be selected from gaseous carbon dioxide, liquid supercritical carbon dioxide and sodium carbonate. In certain such embodiments, such a water presence can be selected from atmospheric water vapor and water applied to such a substrate.

In certain embodiments, such a carbonatable calcium precursor can be treated with sodium hydroxide to provide calcium hydroxide. Carbonation with a carbon dioxide source can then convert calcium hydroxide to calcium carbonate. Regardless, such a bone void filler substrate can comprise materials of the sort discussed above or illustrated elsewhere herein.

In part, the present invention can also be directed to a method of using comparative calcium salt solubilities to prepare a bone void filler substrate comprising calcium particles thereon. Such a method can comprise providing a calcium salt precursor component having a water solubility; applying such a precursor component to a bone void filler substrate; and treating such an applied precursor component with a transformation component selected from alkali metal hydroxide and alkali metal carbonate components to provide on such a substrate a calcium component having a water solubility less than the water solubility of such a precursor component, such a calcium component as can be selected from calcium hydroxide and calcium carbonate particles.

Such a precursor component can be selected from calcium chloride, calcium oxide and calcium acetate. In certain embodiments, transformation with an alkali metal carbonate component (e.g., without limitation, sodium carbonate) can provide desired calcium carbonate particles on such a substrate. In certain other embodiments, transformation with an alkali metal hydroxide component (e.g., without limitation, sodium hydroxide) can provide less water soluble calcium hydroxide particles on such a substrate. In certain such embodiments, subsequent contact of such a substrate with a carbon dioxide source of the sort discussed above, optionally in the presence of water, can convert at least a portion of such calcium hydroxide to calcium carbonate particles on such a substrate.

Accordingly, the present invention can be, in part, directed to a composition resulting from the present methodology. Such a composition can comprise a biocompatible substrate component and discrete particles of calcium carbonate thereon. In certain embodiments, such a substrate can be a bone void filler component comprising one or more materials of the sort discussed above or illustrated elsewhere herein. In certain such embodiments, such calcium carbonate particles can have a micro- or nanocrystalline morphology, such particles as can be on, bound and/or coupled to a surface of such a substrate component. Regardless, a surface of such a substrate component can be porous, and such calcium carbonate particles and/or crystals can be present therein. As contemplated in conjunction with the methodologies of this invention, such a composition can be employed for application as a bone void filler scaffold, positioned within or over a gap or void in bone tissue and used to promote bone growth and healing.

DETAILED DESCRIPTION OF CERTAIN EMBODIMENTS

As demonstrated by certain non-limiting embodiments, the present invention provides a method to form particles or crystals of calcium carbonate dispersed about the surface (including inside pores) of a biocompatible BVF substrate, such as but not limited to a bone implant. As such, fabrication is simplified and scaffold effectiveness is increased because the material is all one phase rather than a mixture of different materials that may segregate.

The calcium carbonate surface treatment of this invention can be applied to substrates comprising materials known to those skilled in the art (e.g., without limitation implant materials) such as calcium salts including but not limited to calcium phosphates (e.g., hydroxyapatite), collagen based materials, anorganic bone, allograft bone, polymers, and metals/alloys. Any such substrate/material coated with precipitated calcium carbonate particles/crystals, as described herein, can be considered in the context of this invention.

Calcium carbonate has a very low solubility (about 0.013 g/1000 ml water), and it is impractical to soak a BVF substrate in a calcium carbonate solution for the purposes of obtaining a coating. A preferred process, in accordance with certain non-limiting embodiments of this invention, starts with a more soluble calcium compound (salt) that is transformed to a calcium carbonate precipitate on a substrate surface. In accordance with broader aspects of this invention, there are many possible routes to obtain this result. The choice of what route to use is limited only by the chemical and/or physical properties of a BVF substrate to be treated.

EXAMPLES OF THE INVENTION

The following non-limiting examples and data illustrate various aspects and features relating to the methods/compositions and/or devices of the present invention, including the preparation of various substrates comprising calcium carbonate coatings. In comparison with the prior art, the present methods, compositions and/or devices provide results and data which are surprising, unexpected and contrary thereto. While the utility of this invention is illustrated through the use of several carbonatable calcium precursor components, BVF substrates and reagents which can be used therewith, it will be understood by those skilled in the art that comparable results are obtainable with various other precursor components, BVF substrates and reagents, as are commensurate with the scope of this invention.

Example 1a

With reference to the equations, below, one approach involves soaking, spraying, or dipping a bone void filler material/substrate in a calcium chloride solution; and soaking dipping, or spraying the calcium chloride wetted substrate with a sodium hydroxide solution to transform the calcium chloride to relatively insoluble calcium hydroxide (and soluble sodium chloride, NaCl). The treated substrate can then be dried (optional) and rinsed with water to remove the NaCl. The final step is to expose the sodium hydroxide treated substrate to a carbon dioxide ($CO_2$) source to transform the hydroxide into carbonate. Alternatively, such a washing step to remove NaCl can be carried out after carbonate transformation. An advantage is that the carbonate is less soluble than the hydroxide, and such an alternative can provide more carbonate on the bone void filler substrate.

Calcium hydroxide has a higher solubility than calcium carbonate, but it is still very low (about 1.8 g/1000 ml water). Calcium chloride has a solubility of about 740 g/1000 ml water which is over 400 times greater than that of calcium hydroxide and so provides a better route than direct treatment with calcium hydroxide to cover the substrate surface with a calcium salt. Sodium hydroxide has a very high water solubility (about 1100 g/1000 cc water), and can be used very sparingly to transform a calcium chloride coated substrate to a calcium hydroxide precipitate coating without washing away much of the calcium chloride. The transformation to carbonate is preferably done by exposure to gaseous $CO_2$, although liquid supercritical $CO_2$ can be used. The surface of the substrate to be treated is preferably damp, or water vapor can be introduced with the $CO_2$ to provide a humid conversion atmosphere.

The end result is a dispersion of nano-sized calcium carbonate crystals over the BVF substrate surface. The surface architecture is unique and cannot be duplicated by depositing a pre-formed calcium carbonate material on the device surface.

Calcium chloride+sodium hydroxide→calcium hydroxide+salt

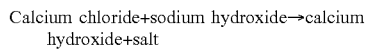

Calcium hydroxide+carbon dioxide→calcium carbonate+water

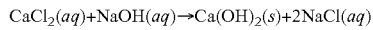

Example 1b

With reference to the preceding, an alternative route uses an organic calcium salt such as calcium acetate (solubility is about 340 g/1000 ml water), followed by treatment with sodium hydroxide to obtain calcium hydroxide and sodium acetate. Carbonation, as described above, provides the desired calcium carbonate particles/crystals.

Example 2

Another approach is to cover a BVF substrate surface with calcium acetate (by soaking, dipping, or spraying a calcium acetate solution), then treating the substrate with a sodium carbonate solution (solubility about 340 g/1000 cc water) to transform the calcium acetate to calcium carbonate and soluble sodium acetate that can be rinsed away.

calcium acetate+sodium carbonate→calcium carbonate+sodium acetate

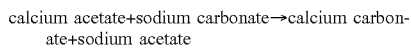

Example 3

Another approach is to cover a BVF substrate surface with calcium chloride (by soaking, dipping, or spraying a calcium chloride solution), then treating the substrate with a sodium carbonate solution to transform the calcium chloride to calcium carbonate along with the formation of soluble sodium chloride that can be rinsed away.

Calcium chloride+sodium carbonate→calcium carbonate+sodium chloride

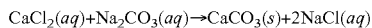

Example 4

Another approach is to transform calcium oxide or another such carbonatable precursor component present in/on a corresponding BVF substrate to calcium carbonate by an aqueous reaction with sodium carbonate. Such a transformation may be a two-step reaction where the calcium oxide is first transformed to calcium hydroxide which then reacts with the sodium carbonate to produce calcium carbonate and sodium hydroxide. The sodium hydroxide is very water soluble and can be rinsed away.

Calcium oxide in water→calcium hydroxide

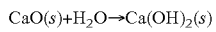

Calcium hydroxide+sodium carbonate→calcium carbonate+sodium hydroxide

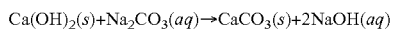

Overall reaction:

Calcium oxide+sodium carbonate→calcium carbonate+sodium chloride

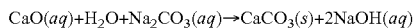

While the principles of this invention have been described in conjunction with certain embodiments, it should be understood clearly that these descriptions are provided only by way of example and are not intended to limit, in any way, the scope of this invention. For instance, in conjunction with comparative carbonate salt solubilities, a transformation component such as an alkali metal hydroxide or carbonate can have a solubility greater than that of a carbonatable calcium precursor component. Likewise, methods and resulting compositions of the present invention can be considered in conjunction with various bone implant materials known to those skilled in the art, including but not limited to a mammalian biocompatible anorganic bone mineral matrix produced by removal of organic components. Alternatively, such substrates can be autologous bone from an implant recipient or allograft bone, such as that obtained from a bone bank. Other advantages and features will become apparent from the claims hereinafter, with the scope of such claims determined by reasonable equivalents as would be understood by those skilled in the art and made aware of this invention.

I claim:

1. A method of preparing discrete calcium carbonate particles on a substrate surface, said method comprising:
   providing a carbonatable calcium precursor component and applying said precursor component to a bone void filler substrate; and
   contacting said substrate with a carbon dioxide source in the presence of water to convert at least a portion of said applied carbonatable calcium precursor component to calcium carbonate and provide discrete calcium carbonate particles on said substrate.

2. The method of claim 1 wherein said precursor component is selected from calcium chloride, calcium oxide and calcium acetate.

3. The method of claim 1 wherein said carbon dioxide source is selected from gaseous carbon dioxide, liquid supercritical carbon dioxide and sodium carbonate.

4. The method of claim 1 wherein said carbonatable calcium precursor component is treated with an alkali metal hydroxide to provide calcium hydroxide.

5. The method of claim 4 wherein said treatment is with sodium hydroxide.

6. The method of claim 1 wherein said carbonatable calcium precursor component is provided as an aqueous solution thereof, and application of said carbonatable calcium precursor component is selected from dipping, soaking and spraying said substrate therewith.

7. The method of claim 1 wherein the presence of water is selected from atmospheric water vapor about said substrate and water applied to said substrate.

8. The method of claim 1 wherein said bone void filler substrate comprises a material selected from calcium salts, collagen, natural mammalian bone, polymers, metals and combinations thereof.

9. The method of claim 1 wherein said substrate is applied to a mammalian bone void.

10. A method of preparing a calcium carbonate surface coating, said method comprising:
    providing a carbonatable calcium precursor component selected from calcium chloride, calcium oxide and calcium acetate, and applying said precursor component to a bone void filler substrate; and
    contacting said substrate with a carbon dioxide source, optionally in the presence of water, to convert at least a portion of said applied carbonatable calcium precursor component to calcium carbonate and provide a coating of discrete, dispersed calcium carbonate particles on said substrate.

11. The method of claim 10 wherein said carbon dioxide source is selected from gaseous carbon dioxide, liquid supercritical carbon dioxide and sodium carbonate.

12. The method of claim 10 wherein said carbonatable calcium precursor component is treated with an alkali metal hydroxide to provide calcium hydroxide.

13. The method of claim 12 wherein said treatment is with sodium hydroxide.

14. The method of claim 10 wherein said carbonatable calcium precursor component is provided as an aqueous solution thereof, and application of said carbonatable calcium precursor component is selected from dipping, soaking and spraying said substrate therewith.

15. The method of claim 10 wherein the presence of water is selected from atmospheric water vapor about said substrate and water applied to said substrate.

16. The method of claim 1 wherein said bone void filler substrate comprises a material selected from calcium salts, collagen, natural mammalian bone, polymers, metals and combinations thereof.

17. The method of claim 10 wherein said substrate is applied to a mammalian bone void.

* * * * *